US006518060B2

(12) United States Patent
Heimberg et al.

(10) Patent No.: US 6,518,060 B2
(45) Date of Patent: Feb. 11, 2003

(54) COVER PAD FOR COVERING A PLURALITY OF REACTION WELLS

(75) Inventors: Wolfgang Heimberg, Ebersberg (DE); Markus Schurf, Siegsdorf (DE)

(73) Assignee: MWG-Biotech AG, Ebersberg (DE)

(*) Notice: Subject to any disclaimer, the term of this patent is extended or adjusted under 35 U.S.C. 154(b) by 113 days.

(21) Appl. No.: 09/754,017

(22) Filed: Apr. 13, 2001

(65) Prior Publication Data

US 2002/0028507 A1 Mar. 7, 2002

(30) Foreign Application Priority Data

Apr. 8, 2000 (DE) .................................... 200 06 546 U

(51) Int. Cl.$^{7}$ ........................... C12M 1/20; C12M 1/38

(52) U.S. Cl. ............................... 435/305.3; 435/287.2; 435/303.1; 220/526; 422/102

(58) Field of Search .......................... 435/283.1, 287.2, 435/288.4, 305.2; 422/102; 220/523, 526

(56) References Cited

U.S. PATENT DOCUMENTS 2,771,399 A * 11/1956 Savage ....................... 422/104
5,056,427 A * 10/1991 Sakabe et al. .............. 100/211
5,282,543 A * 2/1994 Picozza et al. ............. 220/255
5,604,130 A 2/1997 Warner et al. ........... 435/286.7
5,721,136 A * 2/1998 Finney et al. ............ 220/359.3
5,851,492 A * 12/1998 Blattner ...................... 220/232
6,153,426 A * 11/2000 Heimberg ................... 215/316

FOREIGN PATENT DOCUMENTS

WO 9926070 5/1999
WO 9961152 12/1999

* cited by examiner

*Primary Examiner*—William H. Beisner
(74) *Attorney, Agent, or Firm*—Rankin, Hill, Porter & Clark LLP

(57) ABSTRACT

The invention relates to a cover pad. It is used for covering a plurality of reaction wells open to the upper surface configured in a plate-shaped body provided for implementing chemical and/or microbiological reactions such as e.g. the PCR process. The cover pad is made of an elastomer, it comprising a soft backing which is provided with a backing plate for stiffening, and the backing plate is curved such that when a compressive load of at least 5 N is applied to the full surface area of the backing plate by a planar compression body the backing plate elastically conforms thereto in assuming a corresponding shape free of curvature. The cover pad can be lifted off from the reaction wells by a low force even when the reactions implemented in the reaction wells create a vacuum.

12 Claims, 3 Drawing Sheets

COVER PAD FOR COVERING A PLURALITY OF REACTION WELLS

Figure 1:
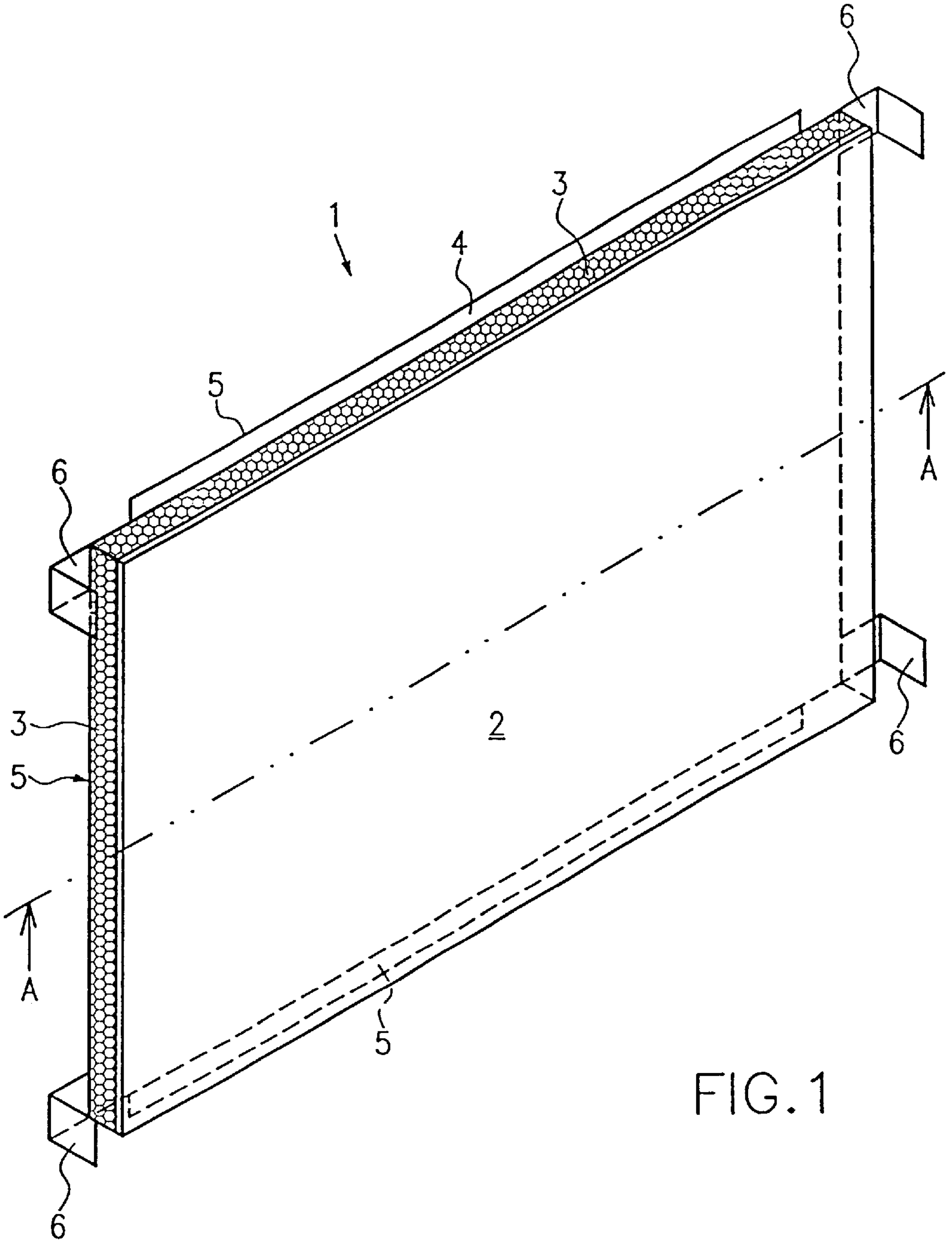

The invention relates to a cover pad for covering a plurality of reaction wells open to the upper surface configured in a plate-shaped body provided for implementing chemical and/or microbiological reactions such as e.g. the PCR process.

The invention is a further development of an in-house earlier development as described in the U.S. patent application THERMOCYCLER APPARATUS (application Ser. No. 09/467,322) filed on Dec. 20, 1999, now U.S. Pat. No. 6,153,426. Reference is made to this patent application in it being incorporated in the present application.

Said patent application relates to a thermocycler apparatus for implementing chemical and biological reactions in which a plate-shaped body can be accommodated comprising reaction wells open to the upper surface. This thermocycler apparatus includes a lid and a closing mechanism for locking the lid in place. An electrically signalled positioner is provided such that once the lid has been locked in place a pressure can be exerted on the reaction wells. For sealing the reaction wells it is proposed to interpose a rubber mat between the the lid and the reaction wells open to the upper surface so that the reaction wells are sealed by the rubber mat which is urged against the reaction wells by the lid.

Conventionally, the reaction wells are sealed by a film of oil or wax. This film of oil or wax is applied to the chemical mixture introduced into the reaction wells and has the task of ensuring that there is no possibility of chemical cross-contamination between neighboring reaction wells. Where chemical or biological reactions are concerned, which take place without any appreciable increase in temperature, it is expedient to apply such a film of oil or wax. Where, however, high reaction temperatures are involved or if the chemical mixture is heated, as is the case with the PCR procedure, for instance, then the oil or wax film becomes thin and no longer represents a suitable protection against chemical cross-contamination between neighboring reaction wells. More particularly, when the chemical mixture boils, the film of oil or wax fails to provide effective contamination protection.

Thus for implementing chemical or biological reactions needing to be free of contamination the reaction wells are welded with a thin film of plastics so that each and every reaction well is closed off. The reaction wells are usually configured in standardized microtitration plates. The film is welded to the microtitration plates such that an annular weld forms around each reaction well.

Providing such a film welded to the reaction wells permits implementing chemical or biological reactions free of contamination. However, prior to implementing the chemical or biological reactions the film needs to be manually welded to the reaction wells and removed manually after the chemical or biological reactions have been carried out. This is why it is hardly possibile to integrate welding such a plastics film in a fully automated system for implementing chemical or biological reactions.

U.S. Pat. No. 5,604,130 describes a pad for covering multi-well plates. This pad is a stiff planar element or a flexible polymer sheet. This polymer sheet may be made of various flexible polymeric materials, e.g. rubber, silicone rubber, polyurethane rubber and the like. The thickness of this sheet is stated to be in the range 0.9 mm to 1.5 mm. The flexible polymer sheet cannot be handled with an automated apparatus since gripping a flexible sheet is very difficult. The planar stiff element is basically suitable for being handled by an automated apparatus. However, such pads prove to be very difficult to release from the reaction wells once the reaction has been implemented, resulting in a vacuum in the individual reaction wells and the apparatus concerned needing to be dimensioned correspondingly large.

Described in WO 99/61152 is another cover for microtitration plates. Shown therein is a multi-layer sheet comprising a backing layer and a sealing layer. The backing layer is stiff. It may, however, be made of a flexible material. The sealing layer is made of a non-elastically deformable material such as e.g. silicone to provide an air-tight seal. This sealing layer comprises a tacky surface so that the the cover tacks to the microtitration plate.

An apparatus for automated implementation of chemical or biological reactions is described in WO 99/26070, it being from this international patent application that the U.S. patent application with application Ser. No. 09/554,743 materialized. Reference is made to this patent application in it being incorporated in the present application.

The invention is based on the object of providing a cover pad for covering a plurality of reaction wells open to the upper surface configured in a plate-shaped body which permits facilitated repeated use in automated systems with no high force needed to lift off the cover pad.

This object of the invention is achieved by a cover pad having the features of claim 1. Advantageous aspects read from the sub-claims.

The cover pad in accordance with the invention is provided for covering a plurality of reaction wells open to the upper surface configured in a plate-shaped body provided for implementing chemical and/or microbiological reactions such as e.g. the PCR process. The cover pad is made of an elastomer, it comprising a soft backing which is provided with a backing plate for stiffening, and the backing plate is curved such that when a compressive load of at least 5 N is applied to the full surface area of the backing plate by a planar compression body the backing plate elastically conforms thereto in assuming a corresponding shape free of curvature.

After the chemical and/or microbiological reactions have been implemented, this curvature of the backing plate results in the cover pad being partially lifted off from the plate-shaped body comprising the reaction wells as soon as a pressure with which the cover pad is urged against the plate-shaped body during the chemical and/or microbiological reaction is cancelled. The backing plate is made of a material which is so stiff that even in the case of reactions, in which a vacuum materializes in the individual reaction wells, the cover pad is lifted off in part from the plate-shaped body. This ensures that no high force is needed to lift off the cover pad from the plate-shaped body even when a vacuum is created in the individual reaction wells. Since the backing plate reassumes its original curvature after the reactions have been implemented, the cover pad has already been released from the majority of the reaction wells and is held only by a few reaction wells arranged in areas at which the curved cover pad is in contact due to the vacuum existing therein. The resulting retaining force is so slight, however, that the cover pad is reliably lifted off from the plate-shaped body when lifted by a handling device.

Figure 2:
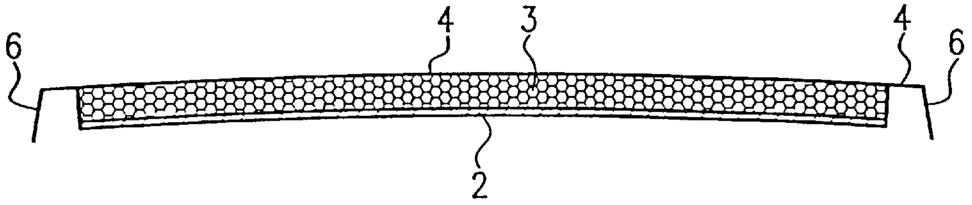
Figure 3:
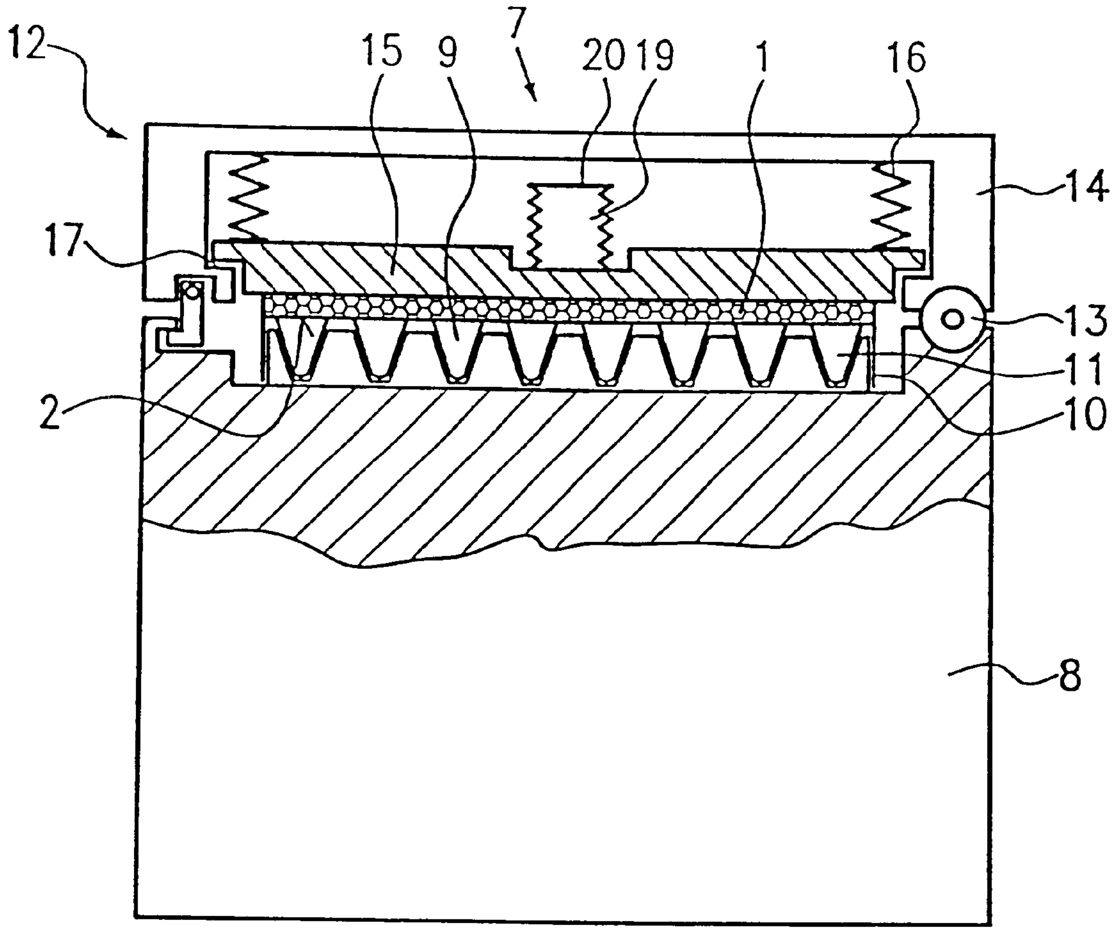
Figure 4:
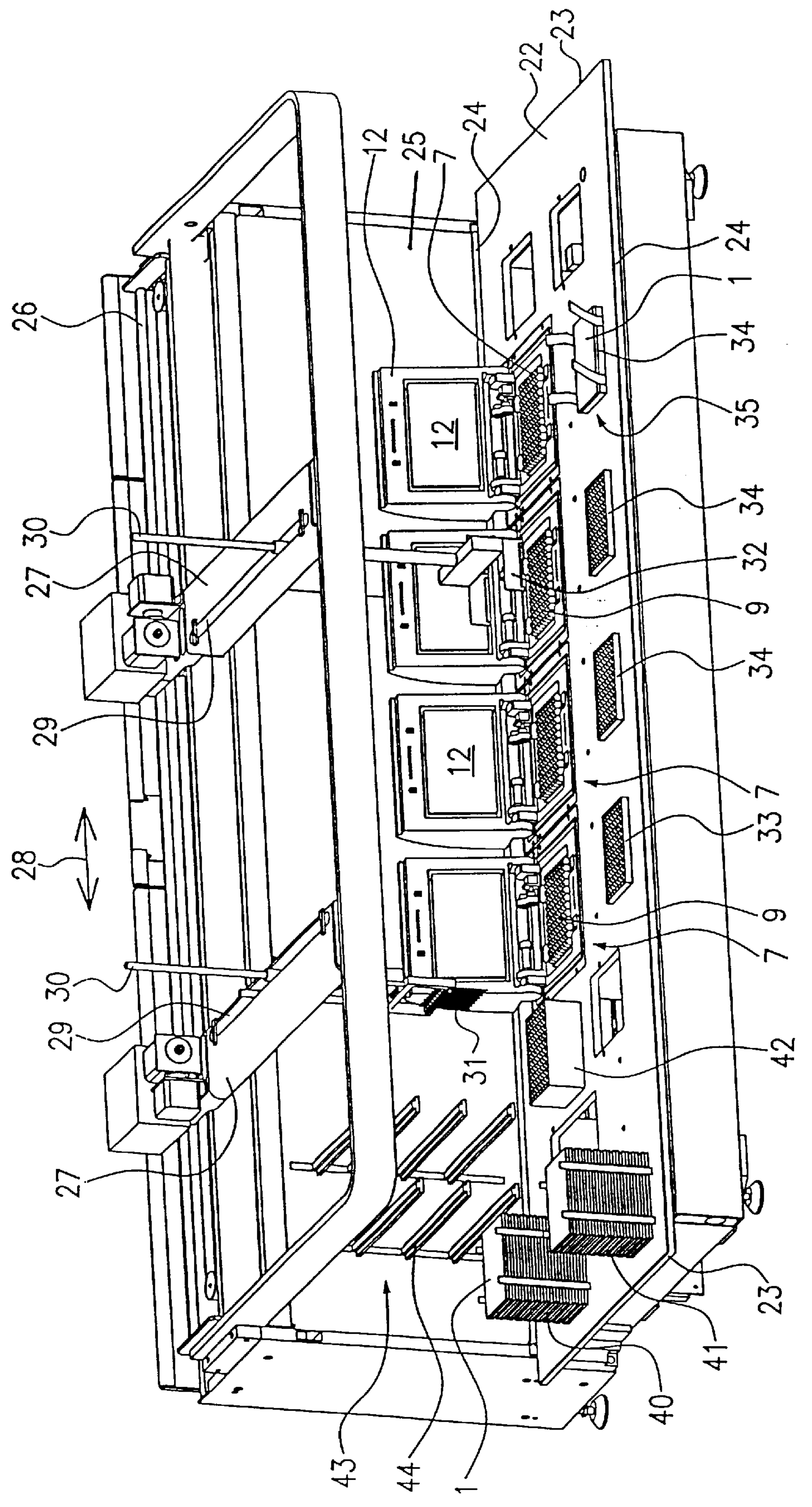

The invention will now be detained by way of an example embodiment with reference to the attached drawings in which:

FIG. 1 is a view in perspective of an example embodiment of the cover pad in accordance with the invention, FIG. 2 is a section taken through the cover pad as shown in FIG. 1 along the line A—A, FIG. 3 is an illustration of a thermocycler apparatus in which the cover pad in accordance with the invention is used, and FIG. 4 is an illustration of an apparatus for automated implementation of chemical and/or microbiological reactions employing the cover pad in accordance with the invention.

DETAILED DESCRIPTION

Referring now to FIG. 1 there is illustrated a view in perspective of an example embodiment of the cover pad in accordance with the invention as viewed from the underside of the cover pad 1 whereas FIG. 2 is a section taken through the cover pad as shown in FIG. 1 along the line A—A.

The face of the cover pad 1 is formed by a cover layer 2 made of a smooth plastics material free of pores and flutings. Experiments have shown that silicone is a material well suited for the cover layer due to its smooth surface finish. The example embodiment as shown in FIGS. 1 and 2 comprises a cover layer of silicone approx. 1 mm thick.

The cover layer 2 is compounded with a compensating layer 3 arranged thereon, cover layer 2 and compensating layer 3 thus forming a composite.

The compensating layer 3 of the example embodiment as shown is 3 mm thick, it being made of a softer material than that of the cover layer 2. The Shore hardness of the compensating layer 3 should not exceed 15°, whereas the cover layer may have a Shore hardness of up to 50°. It is good practice when the Shore hardness of the cover layer 2 is in the range 20° to 40°.

The compensating layer in the present example embodiment is made of expanded silicone, although it could also be made of any other similar expanded elastomer such as e.g. sponge rubber, foamed neoprene or the like.

The cover layer 2 and the compensating layer 3 are sheeted together by vulcanizing or cold curing.

The compensating layer 3 is made preferably of a flexible expanded plastics material permitting the cover pad 1 to be squeezed considerably when compressed.

The compensating layer 3 is secured to a backing plate 4, for example, by bonding. The backing plate 4 is made of a thin sheet of aluminum.

As viewed from above the cover pad is roughly rectangular in shape. The length of the short side edge of the cover layer 2 and of the compensating layer 3 is approx. 7.5 cm and the length of the long side edge approx. 11.5 cm. The backing plate 4 protrudes somewhat at the long sides edges of the cover layer 2 and compensating layer 3. The backing plate 4 thus comprises ledges 5 protruding from the cover layer 2 and compensating layer 3. Molded at short side edges of the cover pad 1 are webs downswept adjoining the corners forming a hook 6. The downswept section of the hook 6 is longer than the overall thickness of the cover layer 2 and compensating layer 3 to thus make sure that when placing the cover pad 1 on a smooth resting surface the cover layer 2 does not come into contact with the resting surface. This avoids contamination of the cover layer 2. The hooks serve furthermore as guide means when arranging the cover pad on a pipetting plate. Such hooks may thus also be provided on the long sides of the cover pad.

The backing plate 4 is curved such that when a compressive load of at least 50 N is applied to the full surface area of the backing plate by a planar compression body the backing plate elastically conforms thereto in assuming a corresponding planar shape free of curvature. Preferably the load for producing the planar shape of the cover pad 1 should be in the range of at least 80 to 100 N.

In the example embodiment as shown in FIGS. 1 and 2 the curvature of the backing plate 4 is configured such that the backing plate 4 is arched, the apex of which is located roughly in the middle portion of the cover pad 1. However, other curvature shapes may be provided within the scope of the invention, for instance, the edge portions of the cover pad 1 may be slightly upswept relative to the middle portion.

Referring now to FIG. 3 there is illustrated the thermocycler apparatus as the basis for detaining the function of the cover pad in accordance with the invention.

This thermocycler apparatus 7 as it reads from the U.S. patent application Ser. No. 09/467,322, now U.S. Pat. No. 6,153,426, comprises a casing 8 serving as the base body configured cuboidal. The upper defining face of the casing 8 serves as the receiving area 9 for receiving a plate-shaped body 10 in which a plurality of reaction wells 11 open to the upper surface are configured. As a rule the plate-shaped body 10 is a pipetting plate 10 or a microtitration plate 10. Such plates are thin-walled plastics parts in which the reaction wells 11 are recessed and arranged in rows and columns. Typically a microtitration plate comprises 24, 48, 96 or 384 reaction wells. Microtitration plates having larger or smaller reaction wells exist, depending on the particular application, the thickness of the individual microtitration plates differing accordingly. The receiving area 9 is provided with dished blind holes open to the upper surface into which each of the reaction wells 11 of the microtitration plate 10 are inserted.

A heating and/or cooling element such as e.g. a Peltier element for heating and cooling the reaction wells 11 may be provided on the receiving area 9. Arranged above the receiving area 9 is a lid 12 which is hinged to the casing 8 by a hinge 13.

The lid is made up of a lid base 14 and a lid segment 15. The lid segment 15 forms advantageously a heating plate which can be heated to a temperature slightly above the maximum reaction temperature generated by the heating and/or cooling element arranged in the receiving area 9. The heating and/or cooling element may cover a temperature profile in the range 0° C. to 95° C., for example, the lid segment 15 then being heated to 100° C., for example, to thus avoid condensation forming on the lid segment.

The lid segment 15 is arranged shiftable along its normals in the lid base 14. Arranged between the upper surface area of the lid segment 15 and the lid base 14 are spring elements 16 which urge the lid segment 15 against a stop 17 of the lid base 14. The spring elements 16 are preloaded by a spring force totalling approx. 20 N, for example.

Arranged in the middle portion between the lid segment 15 and the lid base 14 is an electrochemical linear motor 19. Such electrochemical linear motors are also termed electrochemical actuators.

When the electrochemical motor is powered, i.e. charged, hydrogen is liberated in the bellows causing the bellows to expand in executing a linear movement. When the bellows is discharged via an electrical resistor the hydrogen gas is chemically bound, resulting in a reduction in the gas volume and the bellows is contracted. Mechanically, the electrochemical linear motor behaves like a pneumatic element, except that no external source of compressed air is required, it being electrically activated instead in attaining three control conditions: charging, holding and discharging.

The electrochemical linear motor 19 is secured at one end to the lid segment 15, whilst its opposite end 20 is freely movable. When the electrochemical linear motor actuates, i.e. expands. the electrochemical linear motor 19 is supported by the lid base 14, it thereby urging the lid segment 15 downwards in the direction of the receiving area 9 of the casing 8.

Inserted in the receiving area 9 is a microtitration plate 10, in the reaction wells 11 of which mixtures of chemical reagents are contained. Located on the microtitration plate 10 is the cover pad 1 in accordance with the invention with its cover layer 2 facing downwards. The lid segment 15 is strongly urged downwards by the electrochemical linear motor 19 such that the cover pad 1 assumes a planar shape.

In this arrangement the cover layer 2 is urged against the edge portions of the reaction wells 11 open to the upper surface so that each individual reaction well 11 is reliably sealed off to thus reliably prevent reagent cross-contamination of the individual reaction mixtures even if the reaction mixtures commence boiling.

By configuring the cover layer 2 and compensating layer 3 as a composite the cover pad 1 has adequate strength so that even when a vacuum occurs in the reaction wells 11 it is not durably plastically deformed, it instead reassuming its original shape once the cover pad 1 is released from the microtitration plate 10.

On completion of the chemical reactions being implemented in the thermocycler apparatus 7 the electrochemical linear motor 19 is discharged so that it contracts and the pressure exerted on the cover pad 1 during implementation of the chemical reactions depleted, after which the lid 12 of the thermocycler apparatus 7 is opened. Due to the curvature of the cover pad 1, the cover pad 1 lifts off from the microtitration plate 10 at its arched portion. Since the backing plate 4 is configured so stiff that at least a force of 50 N, preferably more than 80 N to 100 N is needed for surface area pressure to the microtitration plate 10 it is lifted off from the microtitration plate 10 with corresponding force. This enables the cover pad 1 to be also released and lift off from the reaction wells 11 in which a vacuum has been created. The cover pad 1 is thus retained by the vacuum effect only at the portions of the microtitration plate 10 on which it has direct contact. The overall resulting tacking forces between the cover pad 1 and the microtitration plate 10 are thus significantly less than if the cover pad 1 were to contact the microtitration plate 10 by its entire surface area. Experience has shown that even when a vacuum is created during the chemical reactions the curved cover pad 1 can be lifted off from the microtitration plate 10 without the microtitration plate 10 being included in the lift-off. This thus makes it possible for the cover pad 1 in accordance with the invention to be handled fully automatically since there is no risk of including the microtitration plate 10 when lifting the cover pad 1 off from the microtitration plate 10.

The cover pad in accordance with the invention can thus be made use of to seal off microtitration plates in apparatuses for automatic implementation of chemical or biological procedures. One such apparatus is shown diagrammatically in FIG. 4.

One such apparatus for implementing chemical or biological reactions comprises a rectangular base plate 22 having two face edges 23 and a front and rear longitudinal edges 24. Arranged on the base plate 22 at the rear longitudinal edges 24 is a rear wall 25. Provided at the upper edge portion is a horizontal rail 26 parallel to the rear longitudinal edges 24 of the base plate 22 in the rear wall 25, two robotic arms 27 being arranged to travel in the longitudinal direction of the rail 26 (double arrow 28, direction X).

The robotic arms 27 are each linear stiff arms arranged parallel to the face edges 23 of the base plate 22, they thus standing perpendicular to the plane of the rear wall 25. Machined in each robotic arm 27 is a longitudinal slot 29, an actuating arm 30 arranged perpendicular to the base plate 22 extending due to each longitudinal slot 29. Each of the actuating arms 30 can be travelled along a rail (not shown) running in the longitudinal direction (direction Y) of the robotic arms 27. In addition the actuating arms can also be travelled in the vertical direction (direction Z). Secured to one of the two actuating arms 30 is a pipette tip array 31 having eight pipette tips, a forked gripper means 32 being secured to the other actuating arm 30. With the gripper means 32 both the microtitration plates and cover pads 1 can be gripped and relocated. The gripper means has two gripper arms each having protuberances jutting inwards with which the ledges 5 of the cover pad 1 can be clasped.

Arranged on the base plate 22 are four thermocyclers 7 illustrated with their receiving area 9 and lids 12 in the hinged-open condition. Likewise arranged on the base plate 22 are a sample tray 33 and two pipetting trays 34. The sample tray 33 and the pipetting trays 34 are trays configured essentially identical on which microtitration plates can be placed. The microtitration plates mounted on the trays 33, 34 are oriented exactly relative to the base plate 22 by the trays 33, 34 so that the location of each reaction well configured in the microtitration plates is precisely defined and can be precisely located by the robotic arms. The pipetting trays 34 define pipetting stations at which pipetting is executed by means of the pipette tip array 31. Provided on the base plate 22 is further a repository 40 accommodating unused cover pads and a repository 41 for receiving used cover pads 1.

The apparatus comprises furthermore a chemicals reservoir 42 with a plurality of wells open to the upper surface with diverse chemicals and a stacker 43 for receiving a plurality of microtitration plates. The stacker 43 is configured by webs 44 protruding vertically from the rear wall 25.

Using the cover pad 1 in accordance with the invention in one such automated apparatus will now be detained. A user places a microtitration plate 10 on to the sample tray 33 with its wells containing the sample substances. These sample substances are admixed with further reagents from the chemicals reservoir 42 either directly on this microtitration plate or on further microtitration plates on the pipetting trays and subjected to chemical and/or biological reactions, such as e.g. the PCR process in one of the thermocyclers 7. For this purpose the individual microtitration plates are removed by the gripper means 32 from the sample tray 33 or from the pipetting trays 34 and inserted into the thermocycler 7. A cover pad 1 is placed on each microtitration plate 10 located in a thermocycler 7, the cover pad 1 being picked from the stack of unused cover pads. Picking and placing the cover pad 1 is likewise done by the gripper means 32. Once one microtitration plate and one cover pad 1 each are located in a thermocycler 7 the motor-powered lid 12 of the corresponding thermocycler 7 is automatically closed and the corresponding process can commence. On conclusion of the chemical or biological process the lids 12 are again opened automatically, each cover pad picked by the gripper means 32 and placed on the stack 41 of used cover pads.

By providing the cover pads 1 in accordance with the invention this apparatus is able to operate fully automatically without the individual reaction wells needing to be sealed manually, e.g. by welding with a film. Merely the used cover pads 1 stacked in the repository 41 need to be removed from time to time and the repository 40 replenished with cleaned cover pads 1. Preferably the curved cover pads as described above are used since, when the reactions have been implemented, they can be lifted off from the microtitration plates even if a vacuum exists in individual reaction wells.

Although the invention has been described by way of example embodiments it is understood, of course, that it is not restricted to the concrete embodiment of the example. Thus, for instance, the cover layer may be configured of a material other than silicone as long as this material is sufficiently smooth for sealing off the reaction wells. The compensating layer must not necessarily consist of an expanded plastics material, as long as it exhibits the necessarily pliancy. The backing plate may be made e.g. of spring steel or some other flexible and preferably heat-conductive material.

What is claimed is:

1. A cover pad for covering a plurality of reaction wells open to the upper surface configured in a plate-shaped body provided for implementing chemical and/or microbiological reactions, said cover pad comprising an elastomer which is provided with a backing plate for stiffening, and said backing plate is curved such that when a compressive load of at least 5 N is applied to the full surface area of said backing plate by a planar compression body said backing plate elastically conforms thereto in assuming a corresponding shape free of curvature and returns to its curved shape when said compressive load is removed.

2. The cover pad as set forth in claim 1 wherein said elastomer is composed of a facing cover layer backed by a compensating layer and said cover layer is made of a non-porous smooth plastics layer and said compensating layer consists of a layer softer than said cover layer and at least 1.5 mm thick and said cover layer and compensating layer being compounded into a composite.

3. The cover pad as set forth in claim 2 wherein the Shore hardness of said cover layer does not exceed 50°.

4. The cover pad as set forth in claim 2 wherein said compensating layer is at least 3 mm thick and said cover layer is not more than 1 mm thick.

5. The cover pad as set forth in claim 2 wherein a compensating layer is made of an expanded plastics material and said cover layer is made of silicone.

6. The cover pad as set forth in claim 1 wherein the curvature of said backing plate is configured such that said backing plate is arched, the apex of which is located roughly in the middle portion of said cover pad.

7. The cover pad as set forth in claim 1 wherein said backing plate is made of sheet aluminum.

8. An apparatus for implementing chemical and/or biological reactions comprising an area for receiving a plate comprising reaction wells open to the upper surface, a cover pad and a pressure element for urging said cover pad with a predefined force, said cover pad being configured for covering a plurality of reaction wells open to the upper surface configured in a plate-shaped body and comprising an elastomer provided with a backing plate for stiffening and said backing plate being curved such that when a compressive load of at least 5 N is applied to the full surface area of said backing plate by a planar compression body said backing plate elastically conforms thereto in assuming a corresponding shape free of curvature and returns to its curved shape when said compressive load is removed.

9. The apparatus as set forth in claim 8 wherein said predefined force exerted by said pressure element amounts to at least 80 N.

10. The apparatus as set forth in claim 8 wherein said plate comprising said sample wells is a microtitration plate.

11. The apparatus as set forth in claim 8 wherein said apparatus is a thermocycler apparatus.

12. The apparatus as set forth in claim 8 wherein said apparatus includes handling elements for automatically handling said cover pad.

* * * * *